(12) United States Patent
Chen et al.

(10) Patent No.: US 12,419,832 B2
(45) Date of Patent: Sep. 23, 2025

(54) INTRATUMORAL DELIVERY OF BORTEZOMIB

(71) Applicant: Cognos Therapeutics, Inc., Los Angeles, CA (US)

(72) Inventors: Thomas Chen, La Canada (CA); Yehoshua Shachar, Santa Monica, CA (US)

(73) Assignee: COGNOS THERAPEUTICS, INC., Los Angeles, CA (US)

( * ) Notice: Subject to any disclaimer, the term of this patent is extended or adjusted under 35 U.S.C. 154(b) by 622 days.

(21) Appl. No.: 16/965,051

(22) PCT Filed: Jan. 29, 2019

(86) PCT No.: PCT/US2019/015634
§ 371 (c)(1),
(2) Date: Jul. 27, 2020

(87) PCT Pub. No.: WO2019/148181
PCT Pub. Date: Aug. 1, 2019

(65) Prior Publication Data
US 2021/0106522 A1    Apr. 15, 2021

Related U.S. Application Data

(60) Provisional application No. 62/623,100, filed on Jan. 29, 2018.

(51) Int. Cl.
| A61K 9/00 | (2006.01) |
| A61K 31/69 | (2006.01) |
| A61K 45/06 | (2006.01) |
| A61M 5/142 | (2006.01) |
| A61P 35/04 | (2006.01) |

(52) U.S. Cl.
CPC ............ *A61K 9/0085* (2013.01); *A61K 31/69* (2013.01); *A61M 5/14276* (2013.01); *A61P 35/04* (2018.01); *A61K 45/06* (2013.01)

(58) Field of Classification Search
CPC ...... A61K 9/0085; A61K 31/69; A61K 45/06; A61P 35/04; A61M 5/14276
See application file for complete search history.

(56) References Cited

U.S. PATENT DOCUMENTS

| 7,799,012 | B2* | 9/2010 | Shachar | ................ A61P 35/00 |
| | | | | 604/509 |
| 7,799,016 | B2* | 9/2010 | Shachar | ............ A61M 5/14276 |
| | | | | 604/890.1 |
| 8,267,905 | B2 | 9/2012 | Lobl et al. | |
| 2009/0318903 | A1 | 12/2009 | Shachar et al. | |
| 2013/0004459 | A1* | 1/2013 | De The | ................ A61K 38/00 |
| | | | | 424/85.7 |
| 2016/0038612 | A1* | 2/2016 | Hoge | ................ A61K 48/0075 |
| | | | | 435/173.6 |

FOREIGN PATENT DOCUMENTS

| CN | 101204365 A | 6/2008 | |
| JP | 2009-523802 A | 6/2009 | |
| WO | WO-2007084541 A2 * | 7/2007 | ........... A61K 31/135 |

OTHER PUBLICATIONS

Weijun Wang et al., ("Intratumoral delivery of bortezomib: impact on survival in an intracranial glioma tumor model," in Journal of Neurosurgery, 128:695-700, Apr. 14, 2017). (Year: 2017).*

Weijun Wang et al., ("Intratumoral delivery of bortezomib: impact on survival in an intracranial glioma tumor model," in Journal of Neurosurgery, 128:695-700, 2018, published online Apr. 14, 2017). (Year: 2018).*

Olson Jeffrey J. et al : "Proteasome Inhibitor Therapy in a Brain Tumor Model" In : "Proteasome Inhibitors in Cancer Therapy", Jan. 1, 2004 (Jan. 1, 2004), Totowa, NJ, XP055839538, ISBN: 978-1-59259-794-9 pp. 161-170, DOI: 10.1007/978-1-59259-794-9 13.

Supplemental Partial European Search Report of corresponding application EP19744229, dated Sep. 29, 2021.

Wang et al., Intratumoral delivery of bortezomib: Impact on survival in an intracranial glioma tumor model, J. Neurosurg. 2018, 128(3):695-700. Epub Apr. 14, 2017.

Rxlist, "Velcade", Aug. 23, 2017 (Aug. 23, 2017) retrieved on Apr. 4, 2019 from https://web.archive.org/web/20170823012028/https://www.rxlist.com/velcade-drug.htm.

International Search Report and Written Opinion of corresponding PCT/US2019/015634, mailed on Jun. 14, 2019.

* cited by examiner

*Primary Examiner* — Blessing M Fubara
(74) *Attorney, Agent, or Firm* — MH2 Technology Law Group LLP (57) ABSTRACT

A method of administering bortezomib into a brain tumor by a pump implanted in a brain of a subject. The method includes administering a drug to a tumor in a central nervous system of a subject, the method comprising, delivering a therapeutically effective amount of the drug into a brain, tumor by a pump implanted in a brain of the subject, wherein administration of the drag to the subject in the central nervous system is contraindicated because of toxicity of the drug.

4 Claims, 6 Drawing Sheets

INTRATUMORAL DELIVERY OF BORTEZOMIB

FIELD OF THE INVENTION

The present invention relates to intratumoral delivery of a drug. The present invention further relates to methods of administering a proteasome inhibitor to a tumor in the central nervous system.

BACKGROUND OF THE INVENTION

Malignant gliomas, the most common form of central nervous system (CNS) cancers, are currently considered essentially incurable. Among the various malignant gliomas, anaplastic astrocytomas (Grade III) and glioblastoma multiforme (GBM; Grade IV) have an especially poor prognosis due to their aggressive growth and resistance to currently available therapies. The present standard of care for malignant gliomas consists of surgery, ionizing radiation, and chemotherapy. Despite recent advances in medicine, the past 50 years have not seen any significant improvement in prognosis for malignant gliomas. Wen et al. Malignant gliomas in adults. *New England J Med.* 359:492-507, 2008. Stupp et al. Radiotherapy plus concomitant and adjuvant temozolomide for glioblastoma. *New England J Med.* 352: 987-996, 2005.

Glioblastoma (GBM) is the most prevalent and the most aggressive form of primary brain tumor.[2] There is currently no effective treatment for this tumor. The current standard of care, which includes surgery, radiation, and chemotherapy, has increased survival to approximately 15 months from time of diagnosis; however, only 10% of patients survive at 5 years postsurgery.[15] The key obstacle to treatment success is tumor recurrence and resistance to further chemotherapy. Repeated surgery and radiation are often not viable options. Traditionally, the options for treating a tumor located in or on the brain include surgery, radiation, chemotherapy, and local intratumoral therapy. Systemic chemotherapy is a viable option as an adjunct to radiation and surgery. However, it is limited in efficacy in brain cancers by: 1) delivery across the blood brain barrier, 2) development of drug resistance by the cancer cells, and 3) systemic side-effects from the chemotherapeutic agent. Because the blood brain barrier is only partially broken down in the presence of a malignant brain tumor, it still impairs the effective delivery and transport of systemic chemotherapy into the brain cancer. Secondly, brain tumors can develop drug resistance. Lastly, chemotherapy is distributed systemically throughout the entire body. Because the whole body of the patient undergoes the treatment (not just the tumor and the tumor related area), undesirable side effects such as nausea, diarrhea, hair loss, and loss of appetite and energy may occur. Some of the side effects are so strong in some patients that chemotherapy is unavailable to them as a treatment and thus decrease their overall chances for survival.

The proteasome inhibitor bortezomib is effective for a variety of tumors, but not for GBM. In 2003 the FDA approved bortezomib (Velcade, Millennium Pharma), the first proteasome inhibitor for therapeutic use.[19] This drug is currently used for the treatment of multiple myeloma and mantle cell lymphoma.[5] The proteasome is an enzyme complex that is the major site of protein degradation, functioning to break down extraneous or abnormal intracellular proteins through selective destruction of these peptides.[1,3,24] This activity is critical for normal cell cycling and a variety of other functions. Inhibition of proteasome activity leads to apoptosis.[13] As a result of increased proapoptotic signaling and decreased prosurvival signaling, bortezomib effectively induces cells to undergo apoptosis.[24] Proteasome inhibitors can cause cell death through the generation of reactive oxygen species, an increase in tumor necrosis factor-related apoptosis-inducing ligand (TRAIL) cell death through DR5 and Fas expression, and an increase in the proapoptotic Bcl-2 proteins Bim and Bad, as well as other cytotoxic mechanisms.[11,13,20] Prior evidence suggests that proteasome inhibition may be selectively cytotoxic for glioma stem-like cells as compared with normal stem cells.[9] Recent studies show that bortezomib induces cytotoxicity in glioma cells in vitro.[25] However, the activity of bortezomib in intracranial tumor models is questionable. Studies have suggested that lack of bortezomib activity with systemic administration may be due to high levels of efflux transporters in the blood-brain barrier (BBB).[22] Thus, the route of bortezomib delivery plays an important role in the drug's efficacy.

However, because of fatal events, intrathecal administration of bortezombib is contraindicated (see, FDA—Accessdata—Reference ID: 3641334). Therefore, it is critical to identify novel therapeutic approaches for the treatment of cancers such as malignant gliomas with therapeutic agents such as bortezomib. These compounds may be administered alone or in combination with other treatment methods including radiation, standard chemotherapy, and surgery.

SUMMARY

The present disclosure provides for a method of administering bortezomib comprising, delivering a therapeutically effective amount of bortezomib into a brain tumor by a pump implanted in a brain of a subject.

Also encompassed by the present disclosure is a method of administering a drug to a central nervous system of a subject, the method comprising, delivering a therapeutically effective amount of the drug into a brain of the subject by a pump implanted in the brain, wherein administration of the drug to the subject in the central nervous system is contraindicated because of toxicity of the drug (as used herein, the term "drug" is used interchangeably with the terms "agent" or "compound").

The present disclosure provides for a method of administering a drug to a tumor in a central nervous system of a subject, the method comprising, delivering a therapeutically effective amount of the drug into a brain tumor by a pump implanted in a brain of the subject, wherein administration of the drug to the subject in the central nervous system is contraindicated because of toxicity of the drug.

In certain embodiments, the toxicity comprises, peripheral neuropathy, hypotension, cardiac toxicity, pulmonary toxicity, thrombocytopenia, neutropenia, hepatic toxicity or combinations thereof.

In certain embodiments, the agent is a proteasome inhibitor. In certain embodiments, the agent is bortezomib, vincristine, methotrexate, BCNU, bleomycin, cytarbine, dacarbazine, diaziquinone, doxorubicin, mitomycin C, and/or ThioTEPA. In one embodiment, the drug is bortezomib.

In one embodiment, the pump is a magnetic breather pump. In another embodiment, the pump is an osmotic pump.

In certain embodiment, the pump is implanted directly within the brain tumor.

In one embodiment, the tumor is a glioblastoma. In one embodiment, the tumor is an intracranial glioma tumor.

The present method may further comprise the step of treating the subject with radiation. The drug may be administered before, during or after radiation.

The present method may further comprise the step of administering to the subject a chemotherapeutic agent. In certain embodiments, the chemotherapeutic agent is selected from the group consisting of a DNA alkylating agent, a topoisomerase inhibitor, an endoplasmic reticulum stress inducing agent, a platinum compound, an antimetabolite, an enzyme inhibitor, and a receptor antagonist.

BRIEF DESCRIPTION OF THE DRAWINGS

FIGS. 2A-2B. Bortezomib decreased subcutaneous tumor progression when administered IV. FIG. 2A: Glioma cells (U251) were implanted subcutaneously into athymic nu/nu mice. Fourteen days later, intravenous treatment was initiated: vehicle treatment (circle); bortezomib (36 µg total) (square). Subsequently animals were left untreated for 14 days. Bortezomib treatment significantly ($p=0.0145$) decreased tumor growth rate.

FIGS. 3A-3B. Bortezomib does not affect intracranial tumor progression when delivered systemically. Human glioma cells U251 (FIG. 3A) or U87 (FIG. 3B) were implanted intracranially; subsequently, mice were given bortezomib (36 µg total) (square) or vehicle (circle) IV. The brain tumor size was monitored by optical imaging weekly, and animal survival data were analyzed by Kaplan-Meier plot. There were no significant differences between bortezomib compared with vehicle saline control.

FIG. 4. Bortezomib (BZM) administered intratumorally (IT) is effective in increasing survival. Glioma cells (U251) were implanted intracranially. After 10 days, animals were treated IT with vehicle; bortezomib IV (36 µg total); bortezomib IT (low dose, 0.36 µg total); bortezomib IT (medium dose, 1.2 µg total); and bortezomib IT (high dose, 3.6 µg total). Local administration of bortezomib delayed tumor progression and significantly increased median survival time (from 23 to 34 and 37 days for medium and high doses, respectively). Statistical analysis showed the p values as follows: vehicle versus bortezomib IV (36 µg total), $p=0.9523$ (not significant); bortezomib IV (3.6 µg) versus bortezomib IT (low dose, 0.36 µg total), $p=0.1104$ (not significant); bortezomib IV (36 µg) versus bortezomib IT (medium dose, 1.2 µg total), $p=0.0005$; and bortezomib IV (36 µg) versus bortezomib IT (high dose, 3.6 µg total), $p=0.0022$. CED=convection-enhanced delivery.

FIG. 5. Bortezomib inhibits proteasome activity in vivo. Animals were treated by intratumorally administration of bortezomib (3.6 µg total) using the Alzet pump. After 5, 7 or 10 days, animals were euthanized, tumor-bearing brains were harvested, and lysates prepared for the proteasome activity assay. Control values were obtained from vehicle-treated brains at 5, 7, and 10 days. The data show that tumor-bearing animals treated with intratumoral bortezomib exhibit significantly reduced proteasome activity: 5 days ($p=0.03$); 7 days ($p=0.03$); and 10 days ($p=0.0048$). The data are presented as the mean value±SD of 2 independent experiments. P values compare vehicle to proteasome activity at different days of treatment.

DETAILED DESCRIPTION OF THE INVENTION

The present disclosure provides for a method of administering bortezomib into a brain tumor by a pump implanted in a brain of a subject.

Also encompassed by the present disclosure is a method of administering a agent to a tumor in a central nervous system of a subject, the method comprising, delivering a therapeutically effective amount of the drug into a brain tumor by a pump implanted in a brain of the subject, wherein administration of the drug to the subject in the central nervous system is contraindicated because of toxicity of the drug.

In certain embodiments, the toxicity comprises, peripheral neuropathy, hypotension, cardiac toxicity, pulmonary toxicity, thrombocytopenia, neutropenia, hepatic toxicity or combinations thereof.

In certain embodiments, the agent is a proteasome inhibitor. In certain embodiments, the agent is bortezomib, vincristine, methotrexate, BCNU, bleomycin, cytarbine, dacarbazine, diaziquinone, doxorubicin, mitomycin C, and/or ThioTEPA. In one embodiment, the drug is bortezomib.

In one embodiment, the pump is a magnetic breather pump. In another embodiment, the pump is an osmotic pump.

In certain embodiment, the pump is implanted directly within the brain tumor.

In one embodiment, the tumor is a glioblastoma. In one embodiment, the tumor is an intracranial glioma tumor.

The present method may further comprise the step of treating the subject with radiation. The drug may be administered before, during or after radiation.

The present method may further comprise the step of administering to the subject a chemotherapeutic agent. In certain embodiments, the chemotherapeutic agent is selected from the group consisting of a DNA alkylating agent, a topoisomerase inhibitor, an endoplasmic reticulum stress inducing agent, a platinum compound, an antimetabolite, an enzyme inhibitor, and a receptor antagonist.

The present disclosure also provides for methods of using the agent to treat a disease, such as CNS tumors. The agent of the present invention may be administered alone, or in combination with radiation, surgery or other chemotherapeutic agents. The agent may also be co-administered with antiviral agents, anti-inflammatory agents or antibiotics. The agents may be administered concurrently or sequentially. The agent of the present invention can be administered before, during or after the administration of the other active agent(s).

The agent of the present invention may be used for the treatment of nervous system cancers, such as a malignant glioma (e.g., astrocytoma, anaplastic astrocytoma, glioblastoma multiforme), retinoblastoma, pilocytic astrocytomas (grade I), meningiomas, metastatic brain tumors, neuroblastoma, pituitary adenomas, skull base meningiomas, and skull base cancer.

Proteasome Inhibitors

The term "proteasome inhibitor", as used herein, refers to compounds which target, decrease or inhibit the activity of the proteasome. In some embodiments, the proteasome inhibitor is selected from bortezomib (Velcade®, PS-341, [(1R)-3-methyl-1-[[(2S)-3-phenyl-2-(pyrazine-2-carbonylamino)propanoyl]amino]butyl]boronic acid), carfilzomib (Kyprolis), disulfiram, epigallocatechin-3-gallate, MLN 341, and salinosporamide A.

Suitable proteasome inhibitors for use in the methods disclosed herein may include but are not limited to peptide boronic acid compounds. NPI-0052 (salinosporamide A analogs), 2-pyrrolidone compounds, epigallocatechin 3-gallate (EGCG) analogs (in particular those analogs that are specific for proteasome inhibition), PR-171, PR-047, epoxomycin analogs, peptide analogs, tetrapeptide derivatives, tyropeptide A analogs, and combinations thereof. In some embodiments, the proteasome inhibitor inhibits one or more enzymatic activities of a proteasome selected from beta1 subunit activity (chymotryptic-like activity), beta2 subunit activity (tryptic-like activity), and beta5 subunit activity (post-glutamyl peptidyl hydrolytic-like activity). One suitable proteasome inhibitor is bortezomib (BZ) or a pharmaceutically acceptable salt thereof, which for example, may be administered to a patient at a dosage of about 0.7 mg/m.sup.2 to about 1.9 mg/m.sup.2. U.S. Pat. No. 9,636,329.

However, broader use of bortezomib to treat cancer appears to be prevented by systemic toxicity. Bortezomib distributes to healthy tissues, causing diarrhea, fatigue, fluid retention, hypokalemia, hyponatremia, hypotension, malaise, nausea, orthostasis, bortezomib-induced peripheral neuropathy (BIPN) and hematologic toxicities, of which thrombocytopenia is the most severe.

Proteosome inhibitors include bortezomib, pharmaceutically acceptable salts thereof, boronate esters thereof, and/or compounds having structure similar to that of bortezomib. Proteasome inhibitors having structure similar to bortezomib include those compounds disclosed in U.S. Pat. Nos. 7,119,080; 6,747,150; 6,617,317; 6,548,668; 6,465,433; 6,297,217; 6,083,903; 5,780,454; 7,422,830; 7,109,323; 6,958,319; 6,713,446; and 6,699,835.

Many proteasome inhibitors with anticancer activity are known in the art, and may be divided according to covalent and non-covalent inhibitors, with the covalent inhibitors further divided into aldehydes, boronates, epoxyketones, beta-lactones, vinyl sulfones, and alpha, beta-unsaturated carbonyls, among others. Examples in the aldehyde class include MG-132, PSI, and fellutamide B. Examples in the boronate class include bortezomib, CEP-18770, MLN2238, and MLN9708. Examples in the epoxyketone class include epoxomicin, carfilzomib (PR-171), NC-005, YU-101, LU-005, YU-102, NC-001, LU-001, NC-022, PR-957 (LMP7), CPSI (beta5), LMP2-sp-ck, BODIPY-NC-001, azido-NC-002, and ONX 0912 (opromozib). Examples in the beta-lactone class include omuralide, PS-519, marizomib, and belactosin A. Examples in the vinyl sulfone class include $^{125}$I-NIP-L$_3$VS, NC-005-VS, and MV151. Kisselev et al. "Proteasome Inhibitors: An Expanding Army Attacking a Unique Target," Chemistry and Biology 19, Jan. 27, 2012, 99-115 (incorporated by reference). U.S. Pat. Nos. 9,597,410; 9,592,247; 7,531,526 and 9,572,854.

Examples of suitable proteasome inhibitors include without limitation the following compounds, as well as pharmaceutically acceptable salts and boronate esters thereof: N-(4-morpholine) carbonyl-beta-(1-naphthyl)-L-alanine-L-leucine boronic acid, N-(8-quinoline) sulfonyl-beta-(1-naphthyl)-L-alanine-L-leucine boronic acid, N-(2-pyrazine) carbonyl-L-phenylalanine-L-leucine boronic acid, L-proline-L-leucine boronic acid, N-(2-quinoline) carbonyl-L-homophenylalanine-L-leucine boronic acid, N-(3-pyridine) carbonyl-L-phenylalanine-L-leucine boronic acid, N-(3-phenylpropionyl)-L-phenylalanine-L-leucine boronic acid, N-(4-morpholine) carbonyl-L-phenylalanine-L-leucine boronic acid, N-(4-morpholine) carbonyl-(O-benzyl)-L-tyrosine-L-leucine boronic acid, N-(4-morpholine) carbonyl-L-tyrosine-L-leucine boronic acid, and N-(4-morpholine) carbonyl-[O-(2-pyridylmethyl)]-L-tyrosine-L-leucine boronic acid.

CNS Tumors

The agent may be used to treat brain tumors and brain metastases.

The agent may be used to treat the central nervous system (CNS) tumors, including, but not limited to, brain tumors, primary CNS tumors, cerebral primary tumors, and spinal cord tumors. The agent may be used to treat cancer outside the brain.

The agent may be used to treat an extracranial tumor, a primary brain tumor or a brain tumor of metastatic origin.

Non-limiting examples of CNS tumors include gliomas, astrocytomas, meningioma, oligodendroglioma and histocytic lymphoma. Gliomas may occur in the cerebral hemispheres of the brain, or in other areas such as the optic nerve, brain stem or cerebellum.

In certain embodiments, the cancers or metastasis to be treated or prevented include, but are not limited to, primary intracranial central nervous system tumors. Primary intracranial central nervous system tumors include glioblastoma multiform; malignant astrocytomas; oligdendroglioma; ependymoma; low-grade astrocytomas; meningioma; mesenchymal tumors; pituitary tumors; pituitary adenomas; nerve sheath tumors such as schwannomas; central nervous system lymphoma; medulloblastoma; primitive neuroectodermal tumors; neuron and neuron/glial tumors; craniopharyngioma; germ cell tumors; and choroid plexus tumors. U.S. Pat. No. 9,713,646.

In other embodiments, the cancers or metastasis to be treated or prevented include, but are not limited to, primary spinal tumors such as schwannoma, meningioma, ependymoma, sarcomas, astrocytoma, gliomas, vascular tumors, chordomas and epidermoids.

Examples of brain cancers include, but are not limited to, glioblastoma, brain stem glioma, hypophtalmic glioma, cerebellar and cerebral astrocytoma, medulloblastoma, ependymoma, as well as neuroectodermal and pineal tumor.

In other embodiments, the cancers or metastasis to be treated or prevented include, but are not limited to, primary tumors responsible for brain metastasis such as lung (both small cell and non-small cell), breast, unknown primary, melanoma, colon, and urinary organ tumors.

In certain embodiments, the brain tumor may be, for example, of a different tissue origin than brain tissue.

The CNS tumor's tissue of origin may include astrocytes, oligodendrocytes, ependyma, neurons, meninges, etc.

Non-limiting examples of CNS tumors include Pilocytic Astrocytoma (PCA), Glioblastoma Multiforme (GBM), Oligodendroglioma, Ependymoma, Medulloblastoma, Meningioma, Anaplastic astrocytoma, Astrocytoma, Central neurocytoma, Choroid plexus carcinoma, Choroid plexus papilloma, Choroid plexus tumor, Dysembryoplastic neuroepithelial tumour, Ependymal tumor, Fibrillary astrocytoma, Giant-cell glioblastoma, Glioblastoma multiforme, Gliomatosis cerebri, Gliosarcoma, Hemangiopericytoma, Medulloblastoma, Medulloepithelioma, Meningeal carcinomatosis, Neuroblastoma, Neurocytoma, Oligoastrocytoma, Oligodendroglioma, Optic nerve sheath meningioma, Pediatric ependymoma, Pilocytic astrocytoma, Pinealoblastoma, Pincocytoma, Pleomorphic anaplastic neuroblastoma, Pleomorphic xanthoastrocytoma, Primary central nervous system lymphoma, Sphenoid wing meningioma, Subependymal giant cell astrocytoma, Subependymoma, Trilateral retinoblastoma. World Health Organization Classification of Tumours of the Central Nervous System, 2016, $4^{th}$ revised edition.

In certain embodiments, the cancers or metastasis to be treated or prevented include, but are not limited to, primary intracranial central nervous system tumors. Primary intracranial central nervous system tumors include glioblastoma multiform; malignant astrocytomas; oligdendroglioma; ependymoma; low-grade astrocytomas; meningioma; mesenchymal tumors; pituitary tumors; nerve sheath tumors such as schwannomas; central nervous system lymphoma; medulloblastoma; primitive neuroectodermal tumors; neuron and neuron/glial tumors; craniopharyngioma; germ cell tumors; and choroid plexus tumors.

The agents of the present invention that may be used for the treatment of nervous system cancers, such as a malignant glioma (e.g., astrocytoma, anaplastic astrocytoma, glioblastoma multiforme), retinoblastoma, pilocytic astrocytomas (grade I), meningiomas, metastatic brain tumors, neuroblastoma, pituitary adenomas, skull base meningiomas, and skull base cancer. As used herein, the term "nervous system tumors" refers to a condition in which a subject has a malignant proliferation of nervous system cells.

Cancers that can be treated by the present compounds include, but are not limited to, lung cancer, car, nose and throat cancer, leukemia, colon cancer, melanoma, pancreatic cancer, mammary cancer, prostate cancer, breast cancer, hematopoietic cancer, ovarian cancer, basal cell carcinoma, biliary tract cancer; bladder cancer; bone cancer; breast cancer; cervical cancer; choriocarcinoma; colon and rectum cancer; connective tissue cancer; cancer of the digestive system; endometrial cancer; esophageal cancer; eye cancer; cancer of the head and neck; gastric cancer; intra-epithelial neoplasm; kidney cancer; larynx cancer; leukemia including acute myeloid leukemia, acute lymphoid leukemia, chronic myeloid leukemia, chronic lymphoid leukemia; liver cancer; lymphoma including Hodgkin's and Non-Hodgkin's lymphoma; myeloma; fibroma, neuroblastoma; oral cavity cancer (e.g., lip, tongue, mouth, and pharynx); ovarian cancer; pancreatic cancer; prostate cancer; retinoblastoma; rhabdomyosarcoma; rectal cancer; renal cancer; cancer of the respiratory system; sarcoma; skin cancer; stomach cancer; testicular cancer; thyroid cancer; uterine cancer; cancer of the urinary system, as well as other carcinomas and sarcomas. U.S. Pat. No. 7,601,355.

The present invention also provides methods of treating CNS disorders, including, without limitation, primary degenerative neurological disorders such as Alzheimer's, Parkinson's, psychological disorders, psychosis and depression. Autism may also be treated by the present compositions and methods. Treatment may consist of the use of a compound of the present invention alone or in combination with current medications used in the treatment of Parkinson's, Alzheimer's, or psychological disorders.

The present invention also provides a method of improving immunomodulatory therapy responses comprising the steps of exposing cells to an effective amount of a compound of the present invention, such as isoperillyl alcohol, before or during immunomodulatory treatment. Preferred immunomodulatory agents are cytokines, such interleukins, lymphokines, monokines, interfereons and chemokines.

Combination Therapy

The agent may be used in combination with radiation therapy. In one embodiment, the present invention provides for a method of treating tumor cells, such as malignant glioma cells, with radiation, where the cells are treated with an effective amount of the agent and then exposed to radiation. Treatment by the compounds of the present invention may be before, during and/or after radiation. For example, the compounds of the present invention may be administered continuously beginning one week prior to the initiation of radiotherapy and continued for two weeks after the completion of radiotherapy. U.S. Pat. Nos. 5,587,402 and 5,602,184.

In one embodiment, the present invention provides for a method of treating tumor cells, such as malignant glioma cells, with chemotherapy, where the cells are treated with an effective amount of the agent, and then exposed to chemotherapy. Treatment by the compounds of the present invention may be before, during and/or after chemotherapy.

The agents can be used in combination with chemotherapeutic agents or other therapeutic agents for treatment of CNS disorders (including, primary degenerative neurological disorders such as Alzheimer's, Parkinson's, multiple sclerosis, Attention-Deficit Hyperactivity Disorder or ADHD, psychological disorders, psychosis and depression), immunotherapeutic agents, angiogenesis inhibitors, and anti-hypertensive agents. Anti-cancer agents that may be used in combination with the agent can have one or more of the following effects on cancer cells or the subject: cell death; decreased cell proliferation; decreased numbers of cells; inhibition of cell growth; apoptosis; necrosis; mitotic catastrophe; cell cycle arrest; decreased cell size; decreased cell division; decreased cell survival; decreased cell metabolism; markers of cell damage or cytotoxicity; indirect indicators of cell damage or cytotoxicity such as tumor shrinkage; improved survival of a subject; or disappearance of markers associated with undesirable, unwanted, or aberrant cell proliferation. U.S. Patent Publication No. 20080275057.

Also encompassed by the present invention are admixtures and/or coformulations of the agent and at least one other therapeutic agent.

Chemotherapeutic agents include, but are not limited to, DNA alkylating agents, topoisomerase inhibitors, endoplasmic reticulum stress inducing agents, a platinum compound, an antimetabolite, vincalkaloids, taxanes, epothilones, enzyme inhibitors, receptor antagonists, tyrosine kinase inhibitors, boron radiosensitizers (i.e. velcade), and chemotherapeutic combination therapies.

Non-limiting examples of DNA alkylating agents are nitrogen mustards, such as Cyclophosphamide (Ifosfamide, Trofosfamide), Chlorambucil (Melphalan, Prednimustine), Bendamustine, Uramustine and Estramustine; nitrosoureas, such as Carmustine (BCNU), Lomustine (Semustine), Fotemustine, Nimustine, Ranimustine and Streptozocin; alkyl sulfonates, such as Busulfan (Mannosulfan, Treosulfan); Aziridines, such as Carboquone, Triaziquone, Triethylenemelamine; Hydrazines (Procarbazine); Triazenes such as Dacarbazine and Temozolomide; Altretamine and Mitobronitol.

Non-limiting examples of Topoisomerase I inhibitors include Campothecin derivatives including SN-38, APC, NPC, campothecin, topotecan, exatecan mesylate, 9-nitrocamptothecin, 9-aminocamptothecin, lurtotecan, rubitecan, silatecan, gimatecan, diflomotecan, extatecan, BN-80927, DX-8951f, and MAG-CPT as described in Pommier Y. (2006) Nat. Rev. Cancer 6(10):789-802 and U.S. Patent Publication No. 200510250854; Protoberberine alkaloids and derivatives thereof including berberrubine and coralyne as described in Li et al. (2000) Biochemistry 39(24):7107-7116 and Gatto et al. (1996) Cancer Res. 15(12):2795-2800; Phenanthroline derivatives including Benzo[i]phenanthridine, Nitidine, and fagaronine as described in Makhey et al. (2003) Bioorg. Med. Chem. 11 (8): 1809-1820; Terbenzimidazole and derivatives thereof as described in Xu (1998) Biochemistry 37(10):3558-3566; and Anthracycline derivatives including Doxorubicin, Daunorubicin, and Mitoxantrone as described in Foglesong et al. (1992) Cancer Chemother. Pharmacol. 30(2):123-125, Crow et al. (1994) J. Med. Chem. 37(19):31913194, and Crespi et al. (1986) Biochem. Biophys. Res. Commun. 136(2):521-8. Topoisomerase II inhibitors include, but are not limited to Etoposide and Teniposide. Dual topoisomerase I and II inhibitors include, but are not limited to, Saintopin and other Naphthecenediones, DACA and other Acridine-4-Carboxamindes, Intoplicine and other Benzopyridoindoles, TAS-103 and other 7H-indeno[2,1-c]Quinoline-7-ones, Pyrazoloacridine, XR 11576 and other Benzophenazines, XR 5944 and other Dimeric compounds, 7-oxo-7H-dibenz[f,ij]Isoquinolines and 7-oxo-7H-benzo[e]pyrimidines, and Anthracenyl-amino Acid Conjugates as described in Denny and Baguley (2003) Curr. Top. Med. Chem. 3(3):339-353. Some agents inhibit Topoisomerase II and have DNA intercalation activity such as, but not limited to, Anthracyclines (Aclarubicin, Daunorubicin, Doxorubicin, Epirubicin, Idarubicin, Amrubicin, Pirarubicin, Valrubicin, Zorubicin) and Antracenediones (Mitoxantrone and Pixantrone).

Examples of endoplasmic reticulum stress inducing agents include, but are not limited to, dimethyl-celecoxib (DMC), nelfinavir, celecoxib, and boron radiosensitizers (i.e. velcade (Bortezomib)).

Platinum based compounds are a subclass of DNA alkylating agents. Non-limiting examples of such agents include Cisplatin, Nedaplatin, Oxaliplatin, Triplatin tetranitrate, Satraplatin, Aroplatin, Lobaplatin, and JM-216. (see McKeage et al. (1997) J. Clin. Oncol. 201:1232-1237 and in general, CHEMOTHERAPY FOR GYNECOLOGICAL NEOPLASM, CURRENT THERAPY AND NOVEL APPROACHES, in the Series Basic and Clinical Oncology, Angioli et al. Eds., 2004).

"FOLFOX" is an abbreviation for a type of combination therapy that is used to treat colorectal cancer. It includes 5-FU, oxaliplatin and leucovorin. Information regarding this treatment is available on the National Cancer Institute's web site, cancer.gov, last accessed on Jan. 16, 2008.

"FOLFOX/BV" is an abbreviation for a type of combination therapy that is used to treat colorectal cancer. This therapy includes 5-FU, oxaliplatin, leucovorin and Bevacizumab. Furthermore, "XELOX/BV" is another combination therapy used to treat colorectal cancer, which includes the prodrug to 5-FU, known as Capecitabine (Xeloda) in combination with oxaliplatin and bevacizumab. Information regarding these treatments are available on the National Cancer Institute's web site, cancer.gov or from 23 the National Comprehensive Cancer Network's web site, nccn.org, last accessed on May 27,2008.

Non-limiting examples of antimetabolite agents include Folic acid based, i.e. dihydrofolate reductase inhibitors, such as Aminopterin, Methotrexate and Pemetrexed; thymidylate synthase inhibitors, such as Raltitrexed, Pemetrexed; Purine based, i.e. an adenosine deaminase inhibitor, such as Pentostatin, a thiopurine, such as Thioguanine and Mercaptopurine, a halogenated/ribonucleotide reductase inhibitor, such as Cladribine, Clofarabine, Fludarabine, or a guanine/guanosine: thiopurine, such as Thioguanine; or Pyrimidine based, i.e. cytosine/cytidine: hypomethylating agent, such as Azacitidine and Decitabine, a DNA polymerase inhibitor, such as Cytarabine, a ribonucleotide reductase inhibitor, such as Gemcitabine, or a thymine/thymidine: thymidylate synthase inhibitor, such as a Fluorouracil (5-FU). Equivalents to 5-FU include prodrugs, analogs and derivative thereof such as 5'-deoxy-5-fluorouridine (doxifluroidine), 1-tetrahydrofuranyl-5-fluorouracil (ftorafur), Capecitabine (Xcloda), S-I (MBMS-247616, consisting of tegafur and two modulators, a 5-chloro-2,4-dihydroxypyridine and potassium oxonate), ralititrexed (tomudex), nolatrexed (Thymitaq, AG337), LY231514 and ZD9331, as described for example in Papamicheal (1999) The Oncologist 4:478-487.

Examples of vincalkaloids, include, but are not limited to Vinblastine, Vincristine, Vinflunine, Vindesine and Vinorelbine.

Examples of taxanes include, but are not limited to docetaxel, Larotaxel, Ortataxel, Paclitaxel and Tesetaxel. An example of an epothilone is iabepilone.

Examples of enzyme inhibitors include, but are not limited to farnesyltransferase inhibitors (Tipifarnib); CDK inhibitor (Alvocidib, Seliciclib); phosphodiesterase inhibitor (Anagrelide; rolipram); IMP dehydrogenase inhibitor (Tiazofurine); and lipoxygenase inhibitor (Masoprocol). Examples of receptor antagonists include, but are not limited to ERA (Atrasentan); retinoid X receptor (Bexarotene); and a sex steroid (Testolactone).

Examples of tyrosine kinase inhibitors include, but are not limited to inhibitors to ErbB: HER1/EGFR (Erlotinib, Gefitinib, Lapatinib, Vandetanib, Sunitinib, Neratinib); HER2/neu (Lapatinib, Neratinib); RTK class III: C-kit (Axitinib, Sunitinib, Sorafenib), FLT3 (Lestaurtinib), PDGFR (Axitinib, Sunitinib, Sorafenib); and VEGFR (Vandetanib, Semaxanib, Cediranib, Axitinib, Sorafenib); bcr-abl (Imatinib, Nilotinib, Dasatinib); Src (Bosutinib) and Janus kinase 2 (Lestaurtinib).

"Lapatinib" (Tykerb®) is a dual EGFR and erbB-2 inhibitor. Lapatinib has been investigated as an anticancer monotherapy, as well as in combination with trastuzumab, capecitabine, letrozole, paclitaxel and FOLFIRI (irinotecan, 5-fluorouracil and leucovorin), in a number of clinical trials. It is currently in phase III testing for the oral treatment of metastatic breast, head and neck, lung, gastric, renal and bladder cancer.

A chemical equivalent of lapatinib is a small molecule or compound that is a tyrosine kinase inhibitor (TKI) or alternatively a HER-1 inhibitor or a HER-2 inhibitor. Several TKIs have been found to have effective antitumor activity and have been approved or are in clinical trials. Examples of such include, but are not limited to, Zactima (ZD6474), Iressa (gefitinib), imatinib mesylate (STI571; Gleevec), erlotinib (OSI-1774; Tarceva), canertinib (CI 1033), semaxinib (SU5416), vatalanib (PTK787/ZK222584), sorafenib (BAY 43-9006), sutent (SUI 1248) and lefltmomide (SU101).

PTK/ZK is a tyrosine kinase inhibitor with broad specificity that targets all VEGF receptors (VEGFR), the platelet-derived growth factor (PDGF) receptor, c-KIT and c-Fms. Drevs (2003) Idrugs 6 (8): 787-794. PTK/ZK is a targeted drug that blocks angiogenesis and lymphangiogenesis by inhibiting the activity of all known receptors that bind VEGF including VEGFR-I (Flt-1), VEGFR-2 (KDR/Flk-1) and VEGFR-3 (Flt-4). The chemical names of PTK/ZK are 1-[4-Chloroanilino]-4-[4-pyridylmethyl] phthalazine Succinate or 1-Phthalazinamine, N-(4-chlorophenyl)-4-(4-pyridinylmethyl)-butanedioate (1:1). Synonyms and analogs of PTK/TK are known as Vatalanib, CGP79787D, PTK787/ZK 222584, CGP-79787, DE-00268, PTK-787, PTK787A, VEGFR-TK inhibitor, ZK 222584 and ZK.

Chemotherapeutic agents that can be used in combination with the agent may also include amsacrine, Trabectedin, retinoids (Alitretinoin, Tretinoin), Arsenic trioxide, asparagine depleter Asparaginase/Pegaspargase), Celecoxib, Demecolcine, Elesclomol, Elsamitrucin, Etoglucid, Lonidamine, Lucanthone, Mitoguazone, Mitotane, Oblimersen, Temsirolimus, and Vorinostat.

The agent may be used in combination with angiogenesis inhibitors. Examples of angiogenesis inhibitors include, but are not limited to, angiostatin, angiozyme, antithrombin III, AG3340, VEGF inhibitors, batimastat, bevacizumab (avastin), BMS-275291, CAI, 2C3, HuMV833 Canstatin, Captopril, carboxyamidotriazole, cartilage derived inhibitor (CDI), CC-5013, 6-O-(chloroacetyl-carbonyl)-fumagillol, COL-3, combretastatin, combretastatin A4 Phosphate, Dalteparin, EMD 121974 (Cilengitide), endostatin, erlotinib, gefitinib (Iressa), genistein, halofuginone hydrobromide, Id1, Id3, IM862, imatinib mesylate, IMC-IC11 Inducible protein 10, interferon-alpha, interleukin 12, lavendustin A, LY317615 or AE-941, marimastat, mspin, medroxpregesterone acetate, Meth-1, Meth-2, 2-methoxyestradiol (2-ME), neovastat, oteopontin cleaved product, PEX, pigment epithelium growth factor (PEGF), platelet factor 4, prolactin fragment, proliferin-related protein (PRP), PTK787/ZK 222584, ZD6474, recombinant human platelet factor 4 (rPF4), restin, squalamine, SU5416, SU6668, SU11248 suramin, Taxol, Tecogalan, thalidomide, thrombospondin, TNP-470, troponin-1, vasostatin, VEG1, VEGF-Trap, and ZD6474.

Non-limiting examples of angiogenesis inhibitors also include, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, pentosan polysulfate, angiotensin II antagonists, cyclooxygenase inhibitors (including non-steroidal anti-inflammatory drugs (NSAIDs) such as aspirin and ibuprofen, as well as selective cyclooxygenase-2 inhibitors such as celecoxib and rofecoxib), and steroidal anti-inflammatoires (such as corticosteroids, mineralocorticoids, dexamethasone, prednisone, prednisolone, methylpred, betamethasone).

Other therapeutic agents that modulate or inhibit angiogenesis and may also be used in combination with the agent include agents that modulate or inhibit the coagulation and fibrinolysis systems, including, but not limited to, heparin, low molecular weight heparins and carboxypeptidase U inhibitors (also known as inhibitors of active thrombin activatable fibrinolysis inhibitor [TAFIa]). U.S. Patent Publication No. 20090328239. U.S. Pat. No. 7,638,549.

Non-limiting examples of the anti-hypertensive agents include angiotensin converting enzyme inhibitors (e.g., captopril, enalapril, delapril etc.), angiotensin II antagonists (e.g., candesartan cilexetil, candesartan, losartan (or Cozaar), losartan potassium, eprosartan, valsartan (or Diovan), termisartan, irbesartan, tasosartan, olmesartan, olmesartan medoxomil etc.), calcium antagonists (e.g., manidipine, nifedipine, amlodipine (or Amlodin), efonidipine, nicardipine etc.), diuretics, renin inhibitor (e.g., aliskiren etc.), aldosterone antagonists (e.g., spironolactone, eplerenone etc.), beta-blockers (e.g., metoprolol (or Toporol), atenolol, propranolol, carvedilol, pindolol etc.), vasodilators (e.g., nitrate, soluble guanylate cyclase stimulator or activator, prostacycline etc.), angiotensin vaccine, clonidine and the like. U.S. Patent Publication No. 20100113780.

Other therapeutic agents that may be used in combination with the agent include, but are not limited to, Sertraline (Zoloft), Topiramate (Topamax), Duloxetine (Cymbalta), Sumatriptan (Imitrex), Pregabalin (Lyrica), Lamotrigine (Lamictal), Valaciclovir (Valtrex), Tamsulosin (Flomax), Zidovudine (Combivir), Lamivudine (Combivir), Efavirenz (Sustiva), Abacavir (Epzicom), Lopinavir (Kaletra), Pioglitazone (Actos), Desloratidine (Clarinex), Cetirizine (Zyrtec), Pentoprazole (Protonix), Lansoprazole (Prevacid), Rebeprazole (Aciphex). Moxifloxacin (Avelox), Meloxicam (Mobic), Dorzolamide (Truspot), Diclofenac (Voltaren), Enlapril (Vasotec), Montelukast (Singulair), Sildenafil (Viagra), Carvedilol (Coreg), Ramipril (Delix).

Administration Routes

Administration of the compounds directly to the nervous system can include, for example, intracranial, intracerebral, intravertebral, intraventricular, intracerebroventricular, intrathecal, intracisternal, intraspinal, and peri-spinal routes of administration. In certain embodiments, the agent is administered by delivery via needles or catheters with or without pump devices. In certain embodiments, the agent is administered by injection or infusion. In one embodiment, the present method comprises directly infusing the tumor with the agent. In one embodiment, intraventricular injection may be facilitated by an intraventricular catheter, for example, attached to a reservoir, such as an Ommaya reservoir.

In certain embodiments, the agent is administered intratumorally.

In certain embodiments, the agent is administered via a mechanical delivery device or an implantable delivery system. The construction and use of mechanical delivery devices for the delivery of pharmaceutical agents is well known in the art. Direct techniques for, for example, administering a drug directly to the brain usually involve placement of a drug delivery catheter into the patient's ventricular system to bypass the blood-brain barrier. U.S. Pat. Nos. 5,011,472 and 9,359,290. WO2004060403.

In certain embodiments, the agent is administered via a pump or other device that releases the agent. In certain embodiments, the agent is administered via a breather pump. In certain embodiments, the agent is administered via a magnetically controlled pump. In certain embodiments, the agent is administered via an implanted magnetic breather pump. U.S. Pat. Nos. 8,323,270; 7,351,239; 7,288,085; and 6,726,678.

In one embodiment, a pump is implanted into the brain of a patient and delivers a dose of the agent at a controlled rate (e.g., corresponding to the specific needs of the patient).

In certain embodiments, the agent is administered via a device that is capable of delivering the agent directly to a tumor located in the brain of a patient.

In one embodiment, a pump is implanted into the tumor resection cavity and delivers a dose of the agent.

In one embodiment, a catheter implanted into a tumor and delivers a dose of the agent. The options for treating a tumor located in or on the brain include surgery, radiation, chemotherapy, and local intratumoral therapy.

Intratumoral administration may include chemotherapy wafers, stereotactic injections, and convection enhanced deliveries. In certain embodiments, convection enhanced delivery via an external micropump is used to increase the circumference of drug delivery. It may be given by an externalized catheter.

In one embodiment, the pump comprises the following components: a proximal head implanted into the tumor, a catheter extending from the proximal head, and an analyzer unit connected to the catheter. The proximal head comprises a catheter inserted into the tumor and/or a magnetic breather pump. Which type of proximal head is employed depends on whether a tumor cavity is available. If a tumor is considered unresectable or if the patient does not want open surgery, only a catheter will be implanted. However, if a resection is performed, then different size magnetic breather pumps can be inserted into the tumor cavity, depending on its volume. In one embodiment, the entire unit is self-contained and entirely internalized.

A multi-delivery catheter can be employed to administer the agent. Conventional catheters used for convection enhanced delivery for brain tumors consist of either a single port in the tip of peritoneal tubing used for ventriculoperitoneal shunts, or a proximal shunt catheter with multiple holes cut within 1 cm of the tip of catheter tip. The multi-delivery catheter may comprise a catheter tip from which a balloon with multiple spines emerges under positive pressure from the pump.

The present method also provides a metronomic continuous delivery of the agent.

For example, the agent can be administered locally to the area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of the primary brain cancer or brain metastasis.

Alternatively, the agent can be administered via a convection-enhanced drug delivery system. In another embodiment, the agent is administered via a convection-enhanced drug delivery system such as that described in U.S. Pat. No. 5,720,720, incorporated by reference herein. Convection-enhanced drug delivery involves positioning the tip of an infusion catheter within a tissue (e.g., brain tissue) and supplying the drug (e.g., the agent) through the catheter while maintaining a positive pressure gradient from the tip of the catheter during infusion. The catheter is connected to a pump which delivers the drug and maintains the desired pressure gradient throughout delivery of the drug. In certain embodiments, drug delivery rates range from about 0.5 to about 4.0 µl/min with infusion distances of about 1 cm or more. This method is particularly useful for the delivery of drugs to the brain and other tissue, particularly solid nervous tissue. In certain embodiments, convection-enhanced drug delivery is used for delivering the agent in combination with a high molecular-weight polar molecule such as growth factors, enzymes, antibodies, protein conjugates and genetic vectors to the brain or other tissue. In these embodiments, inflow rates can be up to about 15.0 µl/min.

The agent can also be delivered in a vesicle, e.g., a liposome.

In certain embodiments, the agent can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled-release system can be placed in proximity of the target of the agent, e.g., the brain, thus requiring only a fraction of the systemic dose (see, e.g., Goodson, in Medical Applications of Controlled Release, supra, vol. 2, pp. 115 138 (1984)). Other controlled-release systems discussed in the review by Langer (Science 249:1527 1533 (1990)) may be used.

The amount of the agent that will be effective in the treatment or prevention of a primary brain cancer or a brain metastasis can be determined by standard clinical techniques. In addition, in vitro or in vivo assays may optionally be employed to help identify optimal dosage ranges. The precise dose to be employed in the compositions will also depend on the route of administration, and the seriousness of the disease or disorder, and should be decided according to the judgment of the practitioner and each patient's circumstances. In certain embodiments, the general range of effective oral administration amounts of the compound is from about 0.5 mg/day to about 5000 mg/day, preferably about 500 mg/day to about 3500 mg/day, more preferably about 1000 mg/day to about 3000 mg/day, more preferably about 1500 mg/day to about 2500 mg/day and most preferably about 2000 mg/day. In another embodiment, effective amounts for intravenous administration are about 10% of an oral dosage amount and effective amounts for convection-enhanced drug administration are about 1% of an oral dosage amount. Of course, it is often practical to administer the daily dose of compound in portions, at various hours of the day. However, in any given case, the amount of compound administered will depend on such factors as the solubility of the active component, the formulation used and the route of administration.

Pharmaceutical compositions of the present invention may be mixed with a pharmaceutical acceptable carrier, adjuvant and/or excipient, according to conventional pharmaceutical compounding techniques. Pharmaceutically acceptable carriers that can be used in the present compositions encompass any of the standard pharmaceutical carriers, such as a phosphate buffered saline solution, water, and emulsions, such as an oil/water or water/oil emulsion, and various types of wetting agents. The compositions can additionally contain solid pharmaceutical excipients such as starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Liquid carriers, particularly for injectable solutions, include water, saline, aqueous dextrose, and glycols. For examples of carriers, stabilizers and adjuvants, see Remington's Pharmaceutical Sciences, edited by E. W. Martin (Mack Publishing Company, 18$^{th}$ ed., 1990). The compositions also can include stabilizers and preservatives.

As used herein, the term "therapeutically effective amount" is an amount sufficient to treat a specified disorder or disease or alternatively to obtain a pharmacological response treating a disorder or disease. Methods of determining the most effective means and dosage of administration can vary with the composition used for therapy, the purpose of the therapy, the target cell being treated, and the subject being treated. Treatment dosages generally may be titrated to optimize safety and efficacy. Single or multiple administrations can be carried out with the dose level and pattern being selected by the treating physician. Suitable dosage formulations and methods of administering the agents can be readily determined by those of skill in the art. For example, the composition is administered at about 0.01 mg/kg to about 200 mg/kg, about 0.1 mg/kg to about 100 mg/kg, or about 0.5 mg/kg to about 50 mg/kg. When the compounds described herein are co-administered with another agent or therapy, the effective amount may be less than when the agent is used alone.

The present compound may be encapsulated in liposomes or microcapsules. A liposome is a vesicle composed of a lipid bilayer membrane and an aqueous interior. The lipid membrane may be made of phospholipids, examples of which include phosphatidylcholine such as lecithin and lysolecithin; acidic phospholipids such as phosphatidylserine and phosphatidylglycerol; and sphingophospholipids such as phosphatidylethanolamine and sphingomyelin. Alternatively, cholesterol may be added. A microcapsule is a particle coated with a coating material. For example, the coating material may consist of a mixture of a film-forming polymer, a hydrophobic plasticizer, a surface activating agent or/and a lubricant nitrogen-containing polymer. U.S. Pat. Nos. 6,313,176 and 7,563,768.

The present compound can be given alone or in combination with other drugs for the treatment of the above diseases for a short or prolonged period of time. The present compositions can be administered to a mammal, preferably a human. Mammals include, but are not limited to, murines, rats, rabbit, simians, bovines, ovine, porcine, canines, feline, farm animals, sport animals, pets, equine, and primates.

The invention also provides a method for inhibiting the growth of a cell in vitro, ex vivo or in vivo, where a cell, such as a cancer cell, is contacted with an effective amount of the present compound as described herein.

Pathological cells or tissue such as hyperproliferative cells or tissue may be treated by contacting the cells or tissue with an effective amount of a composition of this invention. The cells, such as cancer cells, can be primary cancer cells or can be cultured cells available from tissue banks such as the American Type Culture Collection (ATCC). The pathological cells can be cells of a systemic cancer, gliomas, meningiomas, pituitary adenomas, or a CNS metastasis from a systemic cancer, lung cancer, prostate cancer, breast cancer, hematopoietic cancer or ovarian cancer. The cells can be from a vertebrate, preferably a mammal, more preferably a human. U.S. Patent Publication No. 2004/0087651. Balassiano et al. (2002) *Intern. J. Mol. Med.* 10:785-788. Thorne, et al. (2004) *Neuroscience* 127:481-496. Fernandes, et al. (2005) *Oncology Reports* 13:943-947. Da Fonseca, et al. (2008) *Surgical Neurology* 70:259267. Da Fonseca, et al. (2008) *Arch. Immunol. Ther. Exp.* 56:267-276. Hashizume, et al. (2008) *Neuroncology* 10:112-120.

In vitro efficacy of the present composition can be determined using methods well known in the art. For example, the cytoxicity of the present compound may be studied by MTT [3-(4,5-dimethylthiazol-2-yl)-2,5-diphenyl tetrazolium bromide] cytotoxicity assay. MTT assay is based on the principle of uptake of MTT, a tetrazolium salt, by metabolically active cells where it is metabolized into a blue colored formazon product, which can be read spectrometrically. *J. of Immunological Methods* 65:55 63, 1983. The cytoxicity of the present compound may be studied by colony formation assay. Functional assays for inhibition of VEGF secretion and IL-8 secretion may be performed via ELISA. Cell cycle block by the present compound may be studied by standard propidium iodide (PI) staining and flow cytometry. Invasion inhibition may be studied by Boyden chambers. In this assay a layer of reconstituted basement membrane, Matrigel, is coated onto chemotaxis filters and acts as a barrier to the migration of cells in the Boyden chambers. Only cells with invasive capacity can cross the Matrigel barrier. Other assays include, but are not limited to, cell viability assays, apoptosis assays, and morphological assays.

The following are examples of the present invention and are not to be construed as limiting.

EXAMPLES

Example 1: Intratumoral Delivery of Bortezomib: Impact on Survival in an Intracranial Glioma Tumor Model OBJECTIVE The goal of this study was to demonstrate that bortezomib can be effective in the orthotopic GBM murine model if the appropriate method of drug delivery is used. In this study the Alzet mini-osmotic pump was used to bring the drug directly to the tumor in the brain, circumventing the blood-brain barrier; thus making bortezomib an effective treatment for GBM.

METHODS The 2 human glioma cell lines, U87 and U251, were labeled with luciferase and used in the subcutaneous and intracranial in vivo tumor models. Glioma cells were implanted subcutaneously into the right flank, or intracranially into the frontal cortex of athymic nude mice. Mice bearing intracranial glioma tumors were implanted with an Alzet mini-osmotic pump containing different doses of bortezomib. The Alzet pumps were introduced directly into the tumor bed in the brain. Survival was documented for mice with intracranial tumors.

RESULTS Glioma cells were sensitive to bortezomib at nanomolar quantities in vitro. In the subcutaneous in vivo xenograft tumor model, bortezomib given intravenously was effective in reducing tumor progression. However, in the intracranial glioma model, bortezomib given systemically did not affect survival. By sharp contrast, animals treated with bortezomib intracranially at the tumor site exhibited significantly increased survival.

CONCLUSIONS Bypassing the blood-brain barrier by using the osmotic pump resulted in an increase in the efficacy of bortezomib for the treatment of intracranial tumors. Thus, the intratumoral administration of bortezomib into the cranial cavity is an effective approach for glioma therapy.

Based on encouraging evidence that bortezomib has limited toxicity,[10] we tested the effects of bortezomib on gliomas in vivo. When administered systemically, bortezomib effectively reduced tumor growth in the rodent subcutaneous tumor model but not in the intracranial tumors. However, when bortezomib was administered intratumorally (IT) in the orthotopic tumor model, this drug was effective. These experiments demonstrate that bortezomib can be used effectively against orthotopic tumors, but only if the mode of delivery bypasses the BBB and the drug is delivered directly to the intracranial tumor.

Methods

Cell Culture and Therapeutic Drugs

Human glioma cells (U87, U251, and LN229) were cultured in DMEM, supplemented with 10% fetal bovine serum and 1% penicillin-streptomycin, and incubated in 5% $CO_2$. Bortezomib (Velcade) was purchased from the University of Southern California/Norris Comprehensive Cancer Center pharmacy. Bortezomib has been approved by the FDA for clinical use. The sterile 14-day Alzet mini-osmotic pump (model 2002) was used in these experiments. The Alzet mini-osmotic pump has a reservoir volume of 200 µl and a delivery rate of 0.5 µl/hour. The brain infusion kit, which includes the pump and distribution tubing, was purchased from DURECT Corporation.

The MTT Assay

Glioma cells (5000 cells/well) were seeded in 96-well plates. After 24 hours, bortezomib was added to the cells at different concentrations, and the cells were incubated for 48 hours. The monotetrazolium (MTT) assay was performed according to the manufacturer's protocol (Calbiochem EMD, Millipore). Absorbance was measured using a microtiter plate reader (Molecular Devices) at 490 nm. Percent viability was calculated relative to untreated control cells. All experiments were performed in triplicate.

In Vivo Procedure for Subcutaneous Tumor Cell Implantation

The animal protocol was approved by the institutional animal care and use committee of the University of Southern California. All mice were maintained in a pathogen-free environment throughout the experiment. For the subcutaneous tumor xenograft model, $5 \times 10^5$ human glioma cells (U87, U251, and LN229) suspended in a volume of 50 µl phosphate-buffered saline were implanted into the right flank of 30 athymic nude mice (Harlan, Inc.). Tumors were palpable approximately 2-3 weeks post-implantation. The animals were divided randomly into 5 groups of 6 mice, and treatment was initiated according to protocol.

In Vivo Procedure for Intracranial Tumor Cell Implantation

Briefly, athymic nude mice were anesthetized with ketamine and xylazine (10 mg/kg) and fixed into a stereotactic head frame (Harvard Apparatus). A 1.5-mm bur hole was drilled 1 mm anterior to the coronal suture on the right hemisphere and 2 mm lateral from the midline. A Hamilton syringe fixed onto the head frame was used to inject human glioma cells ($2 \times 10^5$ cells/5 µl) into the right frontal lobe of the brain. The skin incision was then closed with 4-0 silk thread. The appropriate medications were provided to reduce pain.

Procedure for Animal Imaging

Seven to 10 days after tumor cell implantation, imaging was used to confirm brain tumor formation. Briefly, mice were anesthetized using 2% isoflurane gas and injected intravenously (IV) with 50 mg/kg of D-Luciferin (Perkin Elmer) and placed into the IVIS Spectrum (Caliper Life Sciences). Analysis was performed with Living Image software (Caliper Life Sciences), in which circular regions of interest drawn over the tumor site were used, and results were reported as total flux (photons/second). Based on total flux, animals were randomly divided into experimental groups.

In Vivo Procedure for Alzet Mini-Osmotic Pump Implantation

Once tumors were identified, approximately 7 days after intracranial tumor cell implantation, Alzet mini-osmotic pumps were filled with the desired dose of reagent and implanted. A plastic tube primed with the agent was used to connect the infusion kit to the brain. The assembled delivery system was stored at 4° C. overnight before implantation. Bortezomib was delivered into the tumor using the Alzet mini-osmotic pumps.

To anchor the pump to the animal, an incision was made in the scalp alongside the previous surgical scar. The caudal edge of the incision was pulled, and the connective tissues were separated. Subsequently a subcutaneous tunnel was prepared. The Alzet mini-osmotic pump was pushed backward to adjust the location of the brain infusion kit directly above the hole in the skull that had been previously drilled for tumor cell implantation. The infusion kit (plastic tubing) was gently inserted into the formed tumor. The plastic platform end was fixed onto the skull by using instant super glue. The area around the skin incision was sterilized and sutured with 4-0 silk thread. The contents of the Alzet mini-osmotic pump were released into the tumor at a rate of 0.5 ml/hour. The treatment groups (6 mice per group) were listed as the following: 1) pump-administered vehicle (saline); 2) bortezomib (0.3 mg/kg=36 µg in total) given by intravenous injection; 3) low-dose bortezomib (0.003 mg/kg=0.36 µg in total) intracranial pump delivery; 4) medium-dose bortezomib (0.01 mg/kg=1.2 µg in total) intracranial pump delivery; and 5) high-dose bortezomib (0.03 mg/kg=3.6 µg in total) intracranial pump delivery. In summary, bortezomib was administered for 14 days, either IV at 0.3 mg/kg twice weekly (total 4 injections in 14 days), or continuously into the intracranial tumor bed by using the Alzet mini-osmotic pump. After the treatment was completed (14 days), animals were left untreated until the appearance of neurological and behavioral abnormalities requiring euthanasia. Animals treated with vehicle received saline by Alzet mini-osmotic pump.

Assay for 20S Proteasome Activity

Brain lysates were prepared by homogenization of tumor-bearing brains in phosphate-buffered saline. Supernatants were collected by centrifugation at 12,000 rpm for 15 minutes at 4° C. Total protein concentration was measured by the BCA protein assay, and 100 µg of total protein was used to measure proteasome activity. The 20S proteasome assay kit (EMD Millipore) was used according to manufacturer's instructions. The assay is based on detection of fluorophore 7-amino-4-methylcoumarin (AMC) after cleavage from the labeled substrate LLVYAMC. The free AMC fluorescence was quantified using 380-nm excitation and 460-nm emission filters.

Histological Investigation

Tissues used for histological investigation were fixed in 10% formalin, embedded in paraffin, and stained with H & E. The antibody TRA-1-85/CD147 (RD Systems) was used to stain for human cells.

Statistical Analysis

Survival data were plotted using the Kaplan-Meier method. The end point analyzed was the number of days of survival, counted from the date on which tumor cells were implanted by intracranial injection. All 30 mice (6 per treatment group) died, and therefore standard methods for uncensored data could be used to compare the treatment groups. Prior to analysis, the end point (number of days surviving) was log-transformed to render the distribution of the data compatible with the assumptions of the normal distribution. The resulting means and confidence intervals were transformed back to the original scale. A 1-way ANOVA (with 5 treatment groups) was used for the overall test for differences. Once the overall F-test indicated that some of the means were different from the others (p=0.004), then selected pairwise comparisons were performed using the Tukey method of adjusting for multiple comparisons. A statistical evaluation result of p<0.05 was considered significant.

Results

Bortezomib is Cytotoxic to Glioma Cells In Vitro

Figure 1:
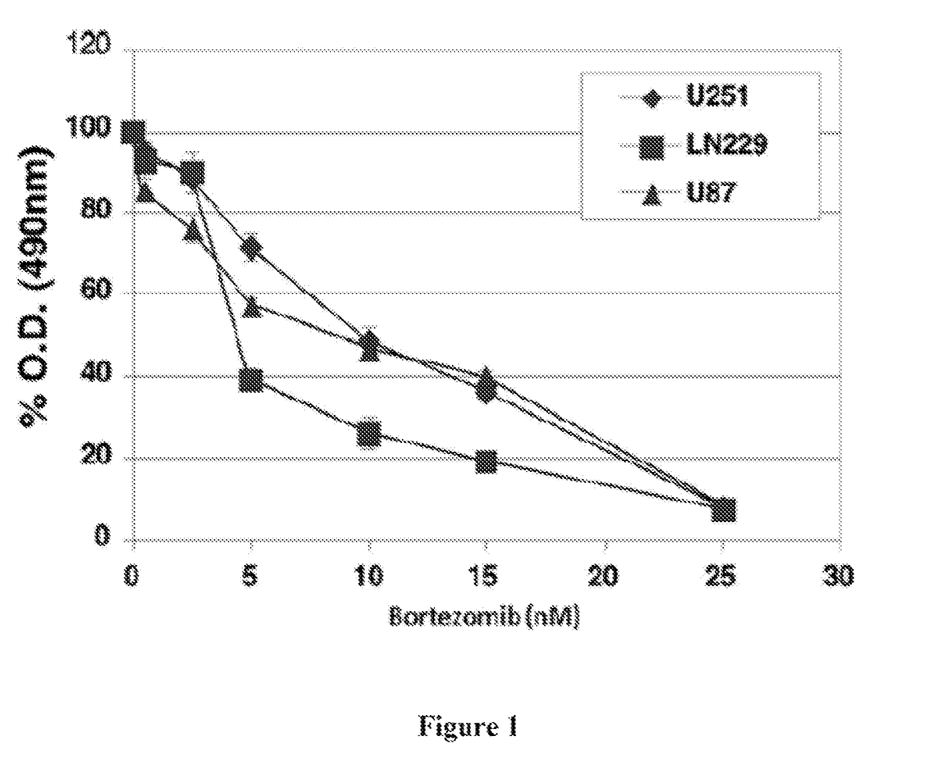
FIG. 1 shows the results of the MTT cytotoxicity assays demonstrating bortezomib is cytotoxic for human glioma cells in vitro. Glioma cells (U251, LN229, U87) were treated with bortezomib (0-25 nM) for 48 hours. Cell death was evaluated using the MTT assay. O.D.=optical density.

To determine whether bortezomib is toxic for glioma cells in vitro, a series of glioma cell lines were treated with bortezomib, at doses ranging from 0 to 25 nM. After 48 hours of incubation, the results (FIG. 1) show that the median inhibitory concentrations (IC50) for the 3 cell lines tested were similar, in the low nanomolar range of 5-10 nM.

Figure 2A:
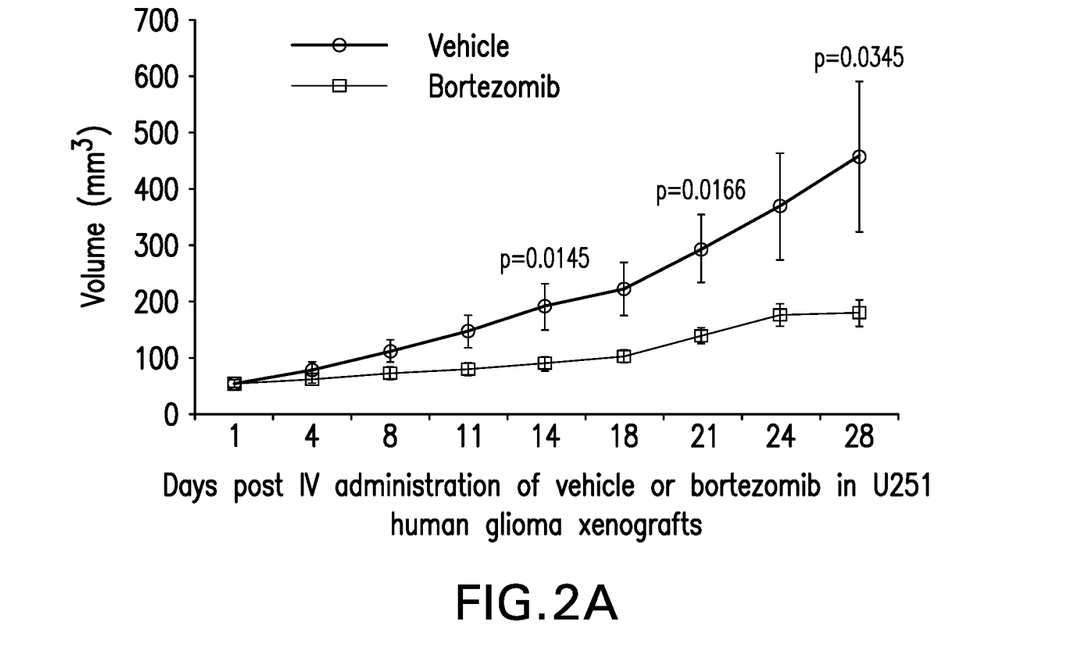

Bortezomib is Effective in Delaying Tumor Growth in the Subcutaneous In Vivo Model To determine whether bortezomib is effective in vivo, the rodent subcutaneous tumor model was used. Tumor cells (U251) were implanted into the right flank. Once tumors were palpable (on approximately Day 15), bortezomib (0.3 mg/kg) was administered IV twice per week. The size of tumors was measured every 3-4 days. The results demonstrate that administration of bortezomib through the intravenous route was significantly effective in delaying tumor growth (p<0.02) (FIG. 2A).

Figure 2B:
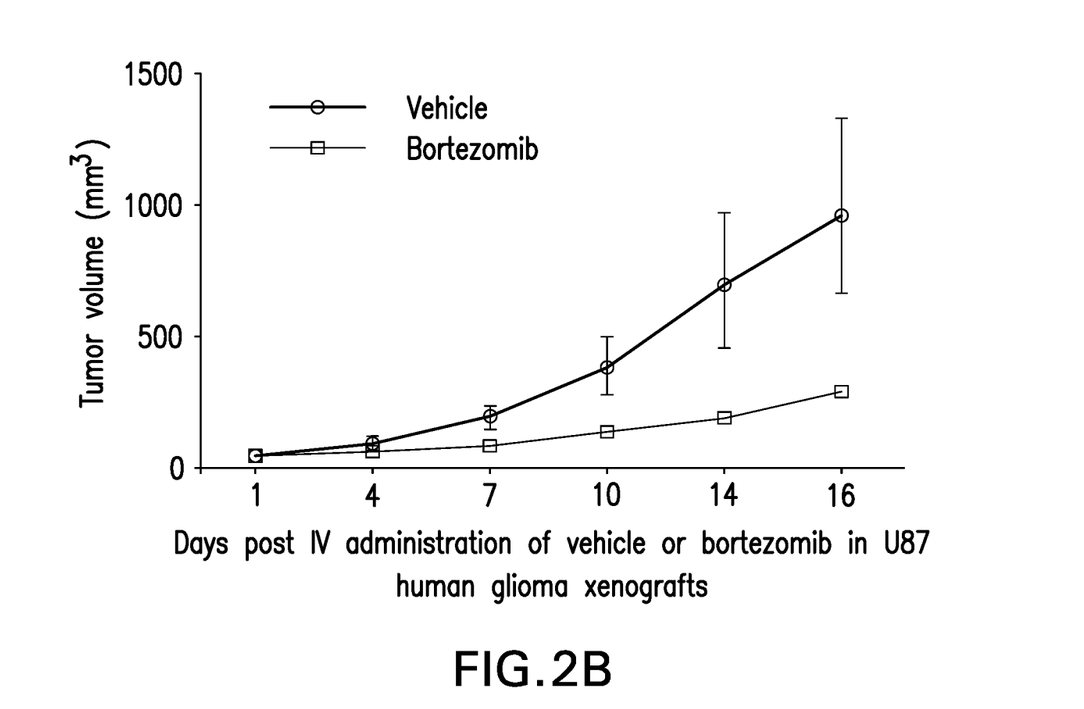
FIG. 2B: Glioma cells (U87) were implanted subcutaneously in athymic nude mice. Bortezomib was administered at a total dose of 36 µg by intravenous injection beginning on Day 30 post-implantation. Bortezomib significantly ($p=0.041$) decreased tumor growth rate for subcutaneous tumors.

To determine whether this response was observed with other glioma cell lines, and using another mode of drug delivery, U87 was tested; here bortezomib (0.3 mg/kg) was administered subcutaneously (FIG. 2B). The results show that in this subcutaneous model, bortezomib delayed tumor progression (p<0.01).

Figure 3A:
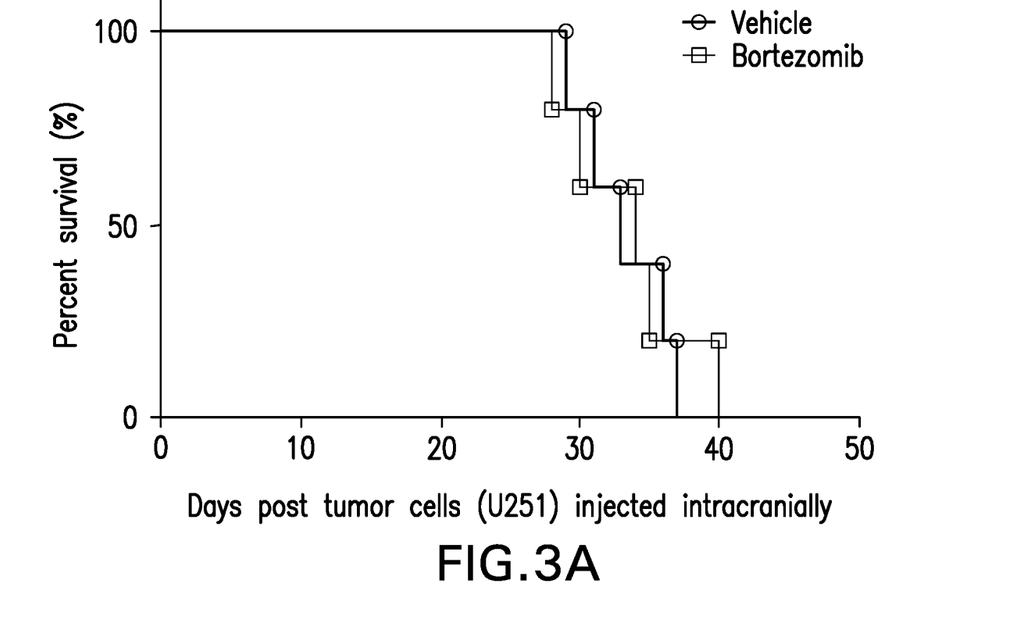
Figure 3B:
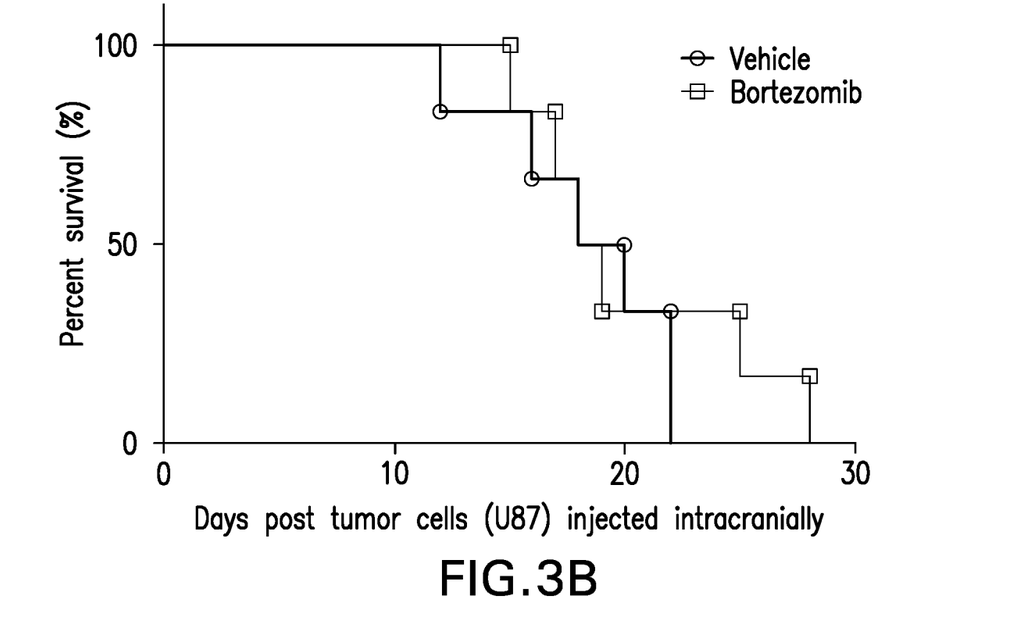

Intravenous Bortezomib is not Effective in the In Vivo Orthotopic Intracranial Glioma Model To determine whether bortezomib can be useful for intracranial glioma therapy using a systemic mode of delivery, this drug was given IV in the orthotopic intracranial glioma model. The U251 glioma cells were implanted into athymic nude mice, and the survival end point was documented. The results (FIG. 3A) showed no significant differences in survival time between IV (0.3 mg/kg) bortezomib-treated animals as compared with the vehicle control. This experiment was repeated using the U87 line, with similar results (FIG. 3B).

Bortezomib is an Effective Drug for Intracranial Tumors when Delivered IT

Figure 4:
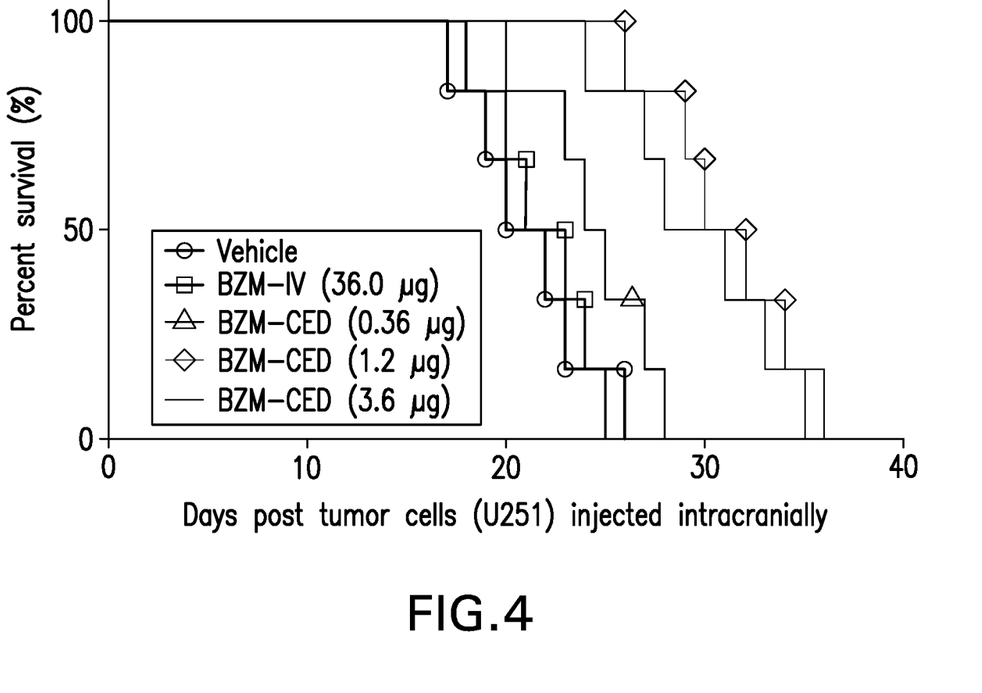
Figure 5:
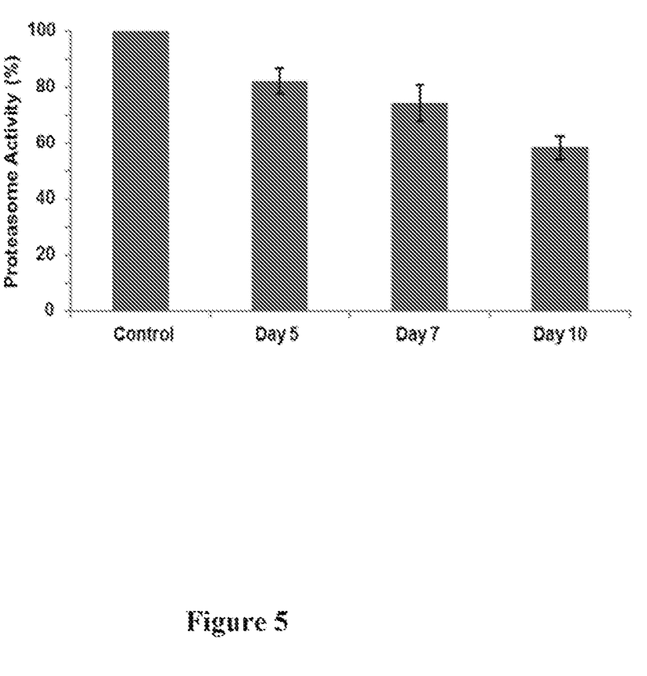

To determine whether the lack of response to bortezomib in the intracranial xenograft model was due to the inability of the drug to enter the brain, we used direct intratumoral delivery of bortezomib. In this procedure, 14-day-delivery Alzet mini-osmotic pumps were implanted into tumor-bearing mice. The pump was used because it is an efficient method for intratumoral administration and circumvents the BBB.[12,21] Furthermore, bortezomib was functioning as a proteasome inhibitor in the brain environment (FIG. 5). The results (FIG. 4) show that for intratumoral delivery compared with intravenous (36 µg) administration, lower intratumoral doses (3.6 µg and 1.2 µg) significantly enhanced survival (p=0.0022 and p=0.0005, respectively). Intratumoral administration of bortezomib increased the median survival time from 23 days to 37 days, providing an approximately 40% increase in survival. Survival of the control animals that received vehicle and the intravenous administration groups were not statistically different. Tumor progression could not be determined using imaging because the pump interfered with imaging.

The doses of bortezomib used in these experiments were determined by injecting escalating doses of the drug intracerebrally (delivered by osmotic mini-pump) into normal, nontumor-bearing mice. Doses of 0.36 µg, 1.2 µg, and 3.6 µg exhibited no toxicity, whereas doses at 7.2 µg. 18.0 µg, and 36.0 µg were toxic and fatal to the testing animals. In FIG. 4, treatment groups (n=6) were vehicle (saline-filled pump); bortezomib given IV (36 µg in total); bortezomib IT (low dose, 0.36 µg); bortezomib IT (medium dose, 1.2 µg); and bortezomib IT (high dose, 3.6 µg). The median survival analysis showed that local administration of bortezomib significantly increased survival time from 23 days to 34 and 37 days for medium and high doses, respectively. The statistical analysis illustrated the p value significance as follows: bortezomib IV (36 µg) versus bortezomib IT (medium dose, 1.2 µg), p=0.0005; and bortezomib IV (36 µg) versus bortezomib IT (high dose, 3.6 µg), p=0.0022. By contrast, for vehicle versus bortezomib IV (36 µg), p=0.9523 (not significant); and for bortezomib IV (36 µg) versus bortezomib IT (0.36 µg, low dose), p=0.1104 (not significant). The results for pump administration of the medium dose (1.2 µg) and the high dose (3.6 µg) of bortezomib were not significantly different, suggesting that the drug concentration may have reached a plateau. Thus, circumventing the BBB by direct intracranial administration of bortezomib is effective for increasing survival of animals bearing intracranial tumors.

DISCUSSION

Effective treatment of GBM is still a challenge, and therefore new drugs and alternative methods of drug delivery must be considered. Bortezomib is a powerful cytotoxic agent, which is functional at nanomolar concentrations. We show here that this powerful agent is also effective against gliomas in vivo, but that the route of administration is critical for drug effectiveness. For intracranial tumors, bortezomib requires intracranial administration.

The requirement for local application of the drug became evident as a result of several in vivo experiments in which varying modes of drug administration were used. In the subcutaneous glioma model, where tumors were implanted into the flank and bortezomib was administered subcutaneously, bortezomib was effective in delaying tumor progression. However, the same dose of bortezomib (36 µg total) delivered subcutaneously to animals bearing an intracranial tumor was not effective. Only bortezomib administered intracranially reduced tumor growth, resulting in a significant increase in survival time. A Phase II trial using the combination of bortezomib and tamoxifen administered systemically to patients with malignant gliomas showed no therapeutic benefit.[14] Based on these and other pharmacokinetic studies,[23] those authors suggest that the BBB may be responsible for the poor penetration of bortezomib into the tumor. Thus, the key to bortezomib activity is bypassing the BBB by direct intracranial administration of the drug. This mode of bortezomib administration is optimal for intracranial tumors.

Bortezomib in combination with other agents has been shown to enhance the drugs' activity in vitro. Bortezomib together with the histone deacetylase inhibitor vorinostat is effective in increasing apoptosis through activating mitochondria in vitro.[18] This drug combination was also tested in vivo in a Phase II clinical trial for treatment of GBM.[8] Bortezomib was administered IV. The trial results demonstrated no benefit, once again showing that systemic delivery of bortezomib is not effective for intracranial tumors. These data and our results indicate that bortezomib should not be used clinically unless the BBB is circumvented.

Figure 6:
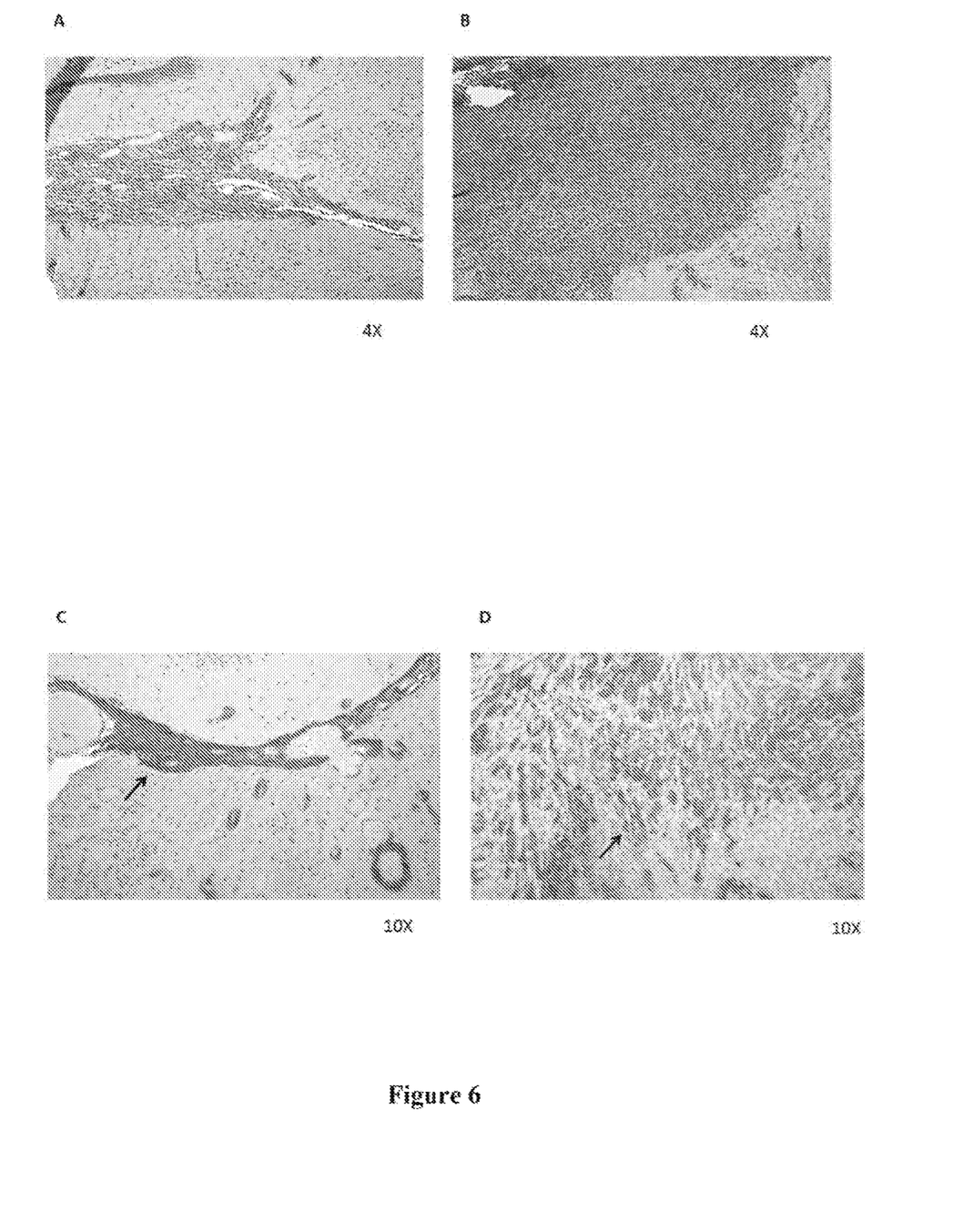
FIG. 6. Histologic analysis demonstrates a smaller tumor in the intratumoral-treated animal compared to the IV-treated animal. Tumor-bearing animals were treated with intratumoral-administered bortezomib (A) or IV-administered-bortezomib (B). After 5 days the animals were euthanized, brains harvested, and stained with hematoxylin/eosin. Based on the surface area, the results show that the tumor in the IV-treated animal was approximately ten-fold larger than the intratumoral-treated animal (4× magnification). Tissues were also stained with anti-human antibody (TRA 1-85); and results showed that IV-treatment resulted in greater tumor cell invasion into mouse brain (arrow) (C), as compared to IT-treated animals (arrow) (D) (10× magnification).

Previous studies have shown that bortezomib is cytotoxic for glioma stem cells, whereas it is not toxic to normal stem cells.[9] The reason for this dichotomy is not clear. A possible explanation may be the result of differences in metabolism and functional levels of proteasomes in glioma stem cells compared with normal stem cells, thus contributing to the increased sensitivity of glioma stem cells. Reports have also indicated that bortezomib, at higher doses, has proangiogenic properties mediated by increased hypoxia-inducible factor-1a and vascular endothelial growth factor.[4] Our in vivo studies showed that microvessel densities in bortezomib-treated animals versus vehicle-treated mice were not significantly different (data not shown). A histological examination of the tissues noted that at Day 5 the tumor in IV treated animals (36 μg total) was larger, as compared with IT treated animals at the higher dose (3.6 μg total). Furthermore, staining these tissues with anti-human cell antibody (TRA 1-85) showed that intravenous treatment resulted in greater tumor cell invasion into mouse brain, compared with IT treated animals. These studies suggest that intratumoral delivery of bortezomib was more effective in reducing tumor progression than intravenous delivery (FIG. 6).

Intracranial administration of bortezomib is effective because it circumvents the BBB. In this study, intracranial drug delivery was used, providing direct access to the brain tumor. The mini-osmotic pump provides drug treatment directly to the brain and also bypasses the liver, thereby achieving the desired drug concentration in the glioma microenvironment while avoiding the use of high drug doses. Other mechanisms of direct drug administration may also be used. Gliadel wafers are FDA approved, and have been shown to be an effective method of local drug administration.[7] The Ommaya reservoir has also been used for intratumoral drug delivery.[16,17] Recently we have demonstrated that an implanted piezoelectric pump can be used in a leptomeningeal carcinomatosis model.[6] Thus, bypassing the BBB is critical and may be accomplished by several techniques.

CONCLUSIONS

These studies demonstrate that bortezomib can be an effective therapy for the treatment of GBM, as long as the drug is administered in such a way that the BBB is circumvented. Using direct intratumoral delivery via an external pump or an implanted pump[6] that will deliver directly to the brain tumor will make bortezomib an effective treatment for gliomas. Our data imply that future clinical studies should not be performed using bortezomib delivered IV for treatment of brain tumors because of the inability of the drug to penetrate the BBB. Our data reveal that circumventing the BBB obstacle via direct local delivery IT is a feasible approach to exploit the therapeutic potential of bortezomib against GBM. Thus, alternative methods of bortezomib delivery can result in increased treatment options for GBM.

REFERENCES

1. Adams J, Palombella V J, Elliott P J: Proteasome inhibition: a new strategy in cancer treatment. Invest New Drugs 18:109-121, 2000
2. Agnihotri S, Burrell K E, Wolf A, Jalali S, Hawkins C, Rutka J T, et al: Glioblastoma, a brief review of history, molecular genetics, animal models and novel therapeutic strategies. Arch Immunol Ther Exp (Warsz) 61:25-41, 2013
3. Boccadoro M, Morgan G, Cavenagh J: Preclinical evaluation of the proteasome inhibitor bortezomib in cancer therapy. Cancer Cell Int 5:18, 2005
4. Bota D A, Alexandru D, Keir S T, Bigner D, Vredenburgh J, Friedman H S: Proteasome inhibition with bortezomib induces cell death in GBM stem-like cells and temozolomideresistant glioma cell lines, but stimulates GBM stem-like cells' VEGF production and angiogenesis. J Neurosurg 119:1415-1423, 2013
5. Buac D, Shen M, Schmitt S, Kona F R, Deshmukh R, Zhang Z, et al: From bortezomib to other inhibitors of the proteasome and beyond. Curr Pharm Des 19:4025-4038, 2013
6. Chen T C, Napolitano G R, Adell F, Schönthal A H, Shachar Y: Development of the Metronomic Biofeedback Pump for leptomeningeal carcinomatosis: technical note. J Neurosurg 123:362-372, 2015
7. Dörner L, Ulmer S, Rohr A, Mehdorn H M, Nabavi A: Spaceoccupying cyst development in the resection cavity of malignant gliomas following Gliadel implantation-incidence, therapeutic strategies, and outcome. J Clin Neurosci 18:347-351, 2011
8. Friday B B, Anderson S K, Buckner J, Yu C, Giannini C, Geoffroy F, et al: Phase II trial of vorinostat in combination with bortezomib in recurrent glioblastoma: a north central cancer treatment group study. Neuro Oncol 14:215-221, 2012
9. Gong X, Schwartz P H, Linskey M E, Bota D A: Neural stem/progenitors and glioma stem-like cells have differential sensitivity to chemotherapy. Neurology 76:1126-1134, 2011
10. Hideshima T, Mitsiades C, Akiyama M, Hayashi T, Chauhan D, Richardson P, et al: Molecular mechanisms mediating antimyeloma activity of proteasome inhibitor PS-341. Blood 101:1530-1534, 2003
11. Kahana S, Finniss S, Cazacu S, Xiang C, Lee H K, Brodie S, et al: Proteasome inhibitors sensitize glioma cells and glioma stem cells to TRAIL-induced apoptosis by PKCe-dependent downregulation of AKT and XIAP expressions. Cell Signal 23:1348-1357, 2011
12. Kawakami K, Kawakami M, Kioi M, Husain S R, Puri R K: Distribution kinetics of targeted cytotoxin in glioma by bolus or convection-enhanced delivery in a murine model. J Neurosurg 101:1004-1011, 2004
13. Ling Y H, Liebes L, Ng B, Buckley M, Elliott P J, Adams J, et al: PS-341, a novel proteasome inhibitor, induces Bcl-2 phosphorylation and cleavage in association with G2-M phase arrest and apoptosis. Mol Cancer Ther 1:841-849, 2002
14. Odia Y, Kreisl T N, Aregawi D, Innis E K, Fine H A: A phase II trial of tamoxifen and bortezomib in patients with recurrent malignant gliomas. J Neurooncol 125:191-195, 2015
15. Omuro A M, Faivre S, Raymond E: Lessons learned in the development of targeted therapy for malignant gliomas. Mol Cancer Ther 6:1909-1919, 2007
16. Oshiro S, Tsugu H, Komatsu F, Ohnishi H, Ueno Y, Sakamoto S, et al: Evaluation of intratumoral administration of tumor necrosis factor-alpha in patients with malignant glioma. Anticancer Res 26 (6A): 4027-4032, 2006
17. Patchell R A, Regine W F, Ashton P, Tibbs P A, Wilson D, Shappley D, et al: A phase I trial of continuously infused intratumoral bleomycin for the treatment of recurrent glioblastoma multiforme. J Neurooncol 60:37-42, 2002
18. Premkumar D R, Jane E P, Agostino N R, DiDomenico J D, Pollack I F: Bortezomib-induced sensitization of malignant human glioma cells to vorinostat-induced apoptosis depends on reactive oxygen species production, mitochondrial dysfunction, Noxa upregulation, Mcl-1 cleavage, and DNA damage. Mol Carcinog 52:118-133, 2013
19. Richardson P G, Mitsiades C, Schlossman R, Ghobrial I, Hideshima T, Munshi N, et al: Bortezomib in the front-line treatment of multiple myeloma. Expert Rev Anticancer Ther 8:1053-1072, 2008
20. Seol D W: p53-Independent up-regulation of a TRAIL receptor DR5 by proteasome inhibitors: a mechanism for proteasome inhibitor-enhanced TRAIL-induced apoptosis. Biochem Biophys Res Commun 416:222-225, 2011
21. van der Bom I M, Moser R P, Gao G, Sena-Esteves M, Aronin N, Gounis M J: Frameless multimodal image guidance of localized convection-enhanced delivery of therapeutics in the brain. J Neurointerv Surg 5:69-72, 2013
22. Veringa S J, Biesmans D, van Vuurden D G, Jansen M H, Wedekind L E, Horsman I, et al: In vitro drug response and efflux transporters associated with drug resistance in pediatric high grade glioma and diffuse intrinsic pontine glioma. PLOS One 8: e61512, 2013
23. Williamson M J, Silva M D, Terkelsen J, Robertson R, Yu L, Xia C, et al: The relationship among tumor architecture, pharmacokinetics, pharmacodynamics, and efficacy of bortezomib in mouse xenograft models. Mol Cancer Ther 8:3234-3243, 2009
24. Yang Y, Yu X: Regulation of apoptosis: the ubiquitous way. FASEB J 17:790-799, 2003
25. Zhang Y, Zhu X, Hou K, Zhao J, Han Z. Zhang X: Mcl-1 downregulation sensitizes glioma to bortezomib-induced apoptosis. Oncol Rep 33:2277-2284, 2015

The scope of the present invention is not limited by what has been specifically shown and described hereinabove. Those skilled in the art will recognize that there are suitable alternatives to the depicted examples of materials, configurations, constructions and dimensions. Numerous references, including patents and various publications, are cited and discussed in the description of this invention. The citation and discussion of such references is provided merely to clarify the description of the present invention and is not an admission that any reference is prior art to the invention described herein. All references cited and discussed in this specification are incorporated herein by reference in their entirety. Variations, modifications and other implementations of what is described herein will occur to those of ordinary skill in the art without departing from the spirit and scope of the invention. While certain embodiments of the present invention have been shown and described, it will be obvious to those skilled in the art that changes and modifications may be made without departing from the spirit and scope of the invention. The matter set forth in the foregoing description and accompanying drawings is offered by way of illustration only and not as a limitation.

What is claimed is:

1. A method of administering bortezomib comprising delivering bortezomib into a brain tumor by a pump implanted in a brain of a subject, wherein the pump consists of a therapeutically effective amount of bortezomib.

2. The method of claim 1, wherein the pump is an osmotic pump.

3. The method of claim 1, wherein the pump is implanted directly within the brain tumor.

4. The method of claim 1, wherein the tumor is an intracranial glioma tumor.

* * * * *